United States Patent
Geladaki

(10) Patent No.: US 12,023,314 B2
(45) Date of Patent: Jul. 2, 2024

(54) ORAL COMPOSITION WITH IMMUNOMODULATING EFFECT ON NATURAL KILLER CELLS

(71) Applicant: Varvara Geladaki, Athens (GR)

(72) Inventor: Varvara Geladaki, Athens (GR)

(*) Notice: Subject to any disclaimer, the term of this patent is extended or adjusted under 35 U.S.C. 154(b) by 141 days.

(21) Appl. No.: 17/178,370

(22) Filed: Feb. 18, 2021

(65) Prior Publication Data

US 2021/0196662 A1 Jul. 1, 2021

Related U.S. Application Data

(63) Continuation of application No. 16/347,648, filed as application No. PCT/GR2017/000064 on Nov. 3, 2017, now abandoned.

(30) Foreign Application Priority Data

Nov. 7, 2016 (GR) .............................. 20160100572

(51) Int. Cl.

| | | |
|---|---|---|
| *A61K 31/202* | (2006.01) | |
| *A61K 9/00* | (2006.01) | |
| *A61K 31/05* | (2006.01) | |
| *A61K 31/194* | (2006.01) | |
| *A61K 31/198* | (2006.01) | |
| *A61K 31/20* | (2006.01) | |
| *A61K 31/201* | (2006.01) | |
| *A61K 31/4415* | (2006.01) | |
| *A61K 31/455* | (2006.01) | |
| *A61K 31/51* | (2006.01) | |
| *A61K 31/525* | (2006.01) | |
| *A61K 31/7004* | (2006.01) | |
| *A61K 33/06* | (2006.01) | |
| *A61K 33/30* | (2006.01) | |
| *A61K 33/32* | (2006.01) | |
| *A61K 33/34* | (2006.01) | |
| *A61P 15/06* | (2006.01) | |
| *A61P 37/06* | (2006.01) | |

(52) U.S. Cl.
CPC .......... *A61K 31/202* (2013.01); *A61K 9/0053* (2013.01); *A61K 31/05* (2013.01); *A61K 31/194* (2013.01); *A61K 31/198* (2013.01); *A61K 31/20* (2013.01); *A61K 31/201* (2013.01); *A61K 31/4415* (2013.01); *A61K 31/455* (2013.01); *A61K 31/51* (2013.01); *A61K 31/525* (2013.01); *A61K 31/7004* (2013.01); *A61K 33/06* (2013.01); *A61K 33/30* (2013.01); *A61K 33/32* (2013.01); *A61K 33/34* (2013.01); *A61P 15/06* (2018.01); *A61P 37/06* (2018.01)

(58) Field of Classification Search
CPC .... A61K 31/047; A61K 31/198; A61K 31/20; A61K 31/201; A61K 31/202; A61K 31/4415; A61K 31/455; A61K 31/51; A61K 31/519; A61K 31/525; A61K 31/593; A61K 31/05; A61K 31/194; A61K 31/7004; A61K 45/06; A61K 9/0053; A61K 9/0095; A61P 15/06; A61P 37/06

See application file for complete search history.

(56) References Cited

U.S. PATENT DOCUMENTS

2015/0025048 A1* 1/2015 Puder ..................... A61P 15/08
                                                                    514/168

FOREIGN PATENT DOCUMENTS

| JP | 2014-136677 A | 7/2014 |
| WO | 2016/113679 A1 | 7/2016 |

OTHER PUBLICATIONS

Elkattan Clinical Trial NCT01916798 Aug. 6, 2013 (Year: 2013).*
Pregnancy Outcome After Intralipid Infusion Among Women Experiencing Recurrent Pregnancy Loss. Poster Presentation, vol. 89, Issue 4, Supplement S11, Apr. 1, 2008, B. Acacio et al.
Intralipid Therapy for Recurrent Pregnancy Loss—Controversies and Future Directions. 34th Annual Meeting of the American Society for Reproductive Immunology, Jun. 2-5, 2014, Jeffrey Braverman, Braverman IVF & Repordutive Immunoolgy, P.C.
How Valuable is Measurement of Peripheral Blood Natural Killer Cells at the Time of Abortion? Nikolaos Paparistidis et al., American Journal of Reproductive Immunology 2008, pp. 306-315.
Notification of Reasons for Rejection, JP Patent No. 2019-546103, dated Aug. 11, 2021.
A.V. Murashko et al., "Omega-3 unsaturated fatty acids during pregnancy: figures and facts" Farmateka, Reviewed Journal for Clinicians, 2015, No. 12, pp. 62-66, See Russian Search.

(Continued)

*Primary Examiner* — Kara R McMillian
(74) *Attorney, Agent, or Firm* — Finch & Maloney PLLC

(57) ABSTRACT

A method of treating recurrent spontaneous abortions or repeated implantation failures in a human female subject, comprising providing a composition including a combination of fatty acids or esters thereof as the active ingredients, wherein the human female subject has at least 12% of peripheral blood NK cells in total peripheral blood cells, and/or the cytotoxicity of the peripheral blood NK cells is at least 10% higher than a mean cytotoxicity of a control population of healthy human females of reproductive age without a reproductive failure and who have given birth to at least one child; orally administering the composition for 15 to 70 days, wherein the total amount of fatty acids or esters, administered per day, is from 0.03 g/kg 1 g/kg of body weight, calculated as fatty acids so as to reduce an immune-mediated sub-fertility for the human female subject.

15 Claims, No Drawings

(56) References Cited

OTHER PUBLICATIONS

Russian Office Action Corresponding to 201911759704 dated Mar. 5, 2021.
Russian Search Report Corresponding to 201911759704 dated Mar. 5, 2021.
Herberman, "Role of Human Natural Killer Cell Responses in Health and Disease", Clinical and Diagnostic Laboratory Immunology, 1994;1:125-33 See Spec., p. 1.
Stites, et al., "Basic and Clinical Immunology", 8th Edition, Appleton and Lange, Norwalk, Conn., 1994 See Spec., p. 1 (To Follow).
Caligiuri, "Human Natural Killer Cells", Blood, Aug. 2008; vol. 112, No. 3 pp. 461-469 See Spec., p. 1.
Moretta et al., "NK Cells at the Interface Between Innate and Adaptive Immunity" Cell Death & Differentiation, 2008; 15:226-33 See Spec., p. 1.
Poli et al., "CD56bright Natural Killer (NK) Cells: An Important NK Cell Subset", Immunology, Apr. 2009; 126(4):458-65 See Spec., p. 2.
Hiby et al., "Human Uterine NK Cells Have a Similar Repertoire of Killer Inhibitory and Activatory Receptors to Those Found in Blood, as Demonstrated by RT-PCR and Sequencing", Molecular Immunology, Apr. 1997; 34(5):419-30 See Spec., p. 2 (To Follow).
Gellersen et al., "Decidualization of the Human Endometrium: Mechanisms, Functions, and Clinical Perspectives" Seminars in Reproductive Medicine, 2007; 25:445-53 See Spec., p. 2 (To Follow).
Santoni et al., "Uterine NK Cell Development, Migration and Function", Reproductive BioMedicine Online, 2008; 16:202-10 See Spec., p. 2 (To Follow).
King et al., "Uterine Leukocytes and Decidualization", Human Reproduction Update, 2000; 6:28-36 See Spec., p. 2 (To Follow).
Ashkar et al., "Interferon γ Contributes to Initiation of Uterine Vascular Modification, Decidual Integrity, and Uterine Natural Killer Cell Maturation During Normal Murine Pregnancy", Journal of Experimental Medicine, 2000; 192:259-70 See Spec., p. 2.
Clark et al., "Psycho-Neuro-Cytokine/Endocrine Pathways in Immunoregulation During Pregnancy", American Journal of Reproductive Immunology, 1996; 35:330-7 See Spec., p. 3 (To Follow).
Chaouat et al., "Immune Suppression and Th1/Th2 Balance in Pregnancy Revisited: A (Very) Personal Tribute to Tom Wegmann", American Journal of Reproductive Immunology, 1997; 37:427-34 See Spec., p. 3 (To Follow).
Labarrere, "Allogenic Recognition and Rejection Reactions in the Placental" American Journal of Reproductive Immunology, 1989; 21:94-9 See Spec., p. 3 (To Follow).
Stern et al., "Current Status of Immunologic Recurrent Pregnancy Loss", Current Opinion in Obstetrics & Gynecology, 1993; 5:252-9 See Spec., p. 3 (To Follow).
King et al., "The Response of Human Decidual Leukocytes to IL-2", Cellular Immunology, 1992; 141:409-42 See Spec., p. 3 (To Follow).
Vassiliadou et al., "Immunohistochemical Evidence for Increased Numbers of "Classic" CD57+ Natural Killer Cells in the Endometrium of Women Suffering Spontaneous Early Pregnancy Loss" Human Reproduction, 1996; 11:1569-74 See Spec., p. 3.
Kwak et al., "Immunopathology of the Implantation Site Utilizing Monoclonal Antibodies to Natural Killer Cells in Women with Recurrent Pregnancy Losses", American Journal of Reproductive Immunology, 1999; 41:91-8 See Spec., p. 3 (To Follow).
Coulam et al., "Systemic CD56+ Cells Can Predict Pregnancy Outcome", American Journal of Reproductive Immunology, 1995; 33:40-6 See Spec., p. 3 (To Follow).
Aoki et al., "Preconceptual Natural Killer Cell Activity as a Predictor of Miscarriage", The Lancet, 1995: 345:1340-2 See Spec., pp. 3 & 4.
Gafter et al., "Suppressed Cell-Mediated Immunity and Monocyte and Natural Killer Cell Activity Following Allogeneic Immunization of Women with Spontaneous Recurrent Abortion", Journal of Clinical Immunology, 1997; 17:408-19 See Spec., p. 4 (To Follow).

Ruiz et al., "Intravenous Immunoglobulin Inhibits Natural Killer Cell Activity in Vivo in Women with Recurrent Spontaneous Abortion" American Journal of Reproductive Immunology, 1996; 35:370-5 See Spec., p. 4 (To Follow).
Stiehm, "Adverse Effects of Human Immunoglobulin Therapy", Transfusion Medicine Reviews, vol. 27, Issue 3, Jul. 2013, pp. 171-178 See Spec., p. 4 (To Follow).
Roussev et al., "Natural Killer cell Functional Activity Suppression by Intravenous Immunoglobulin, Intralipid and Soluable Human Leukocyte Antigen-G", American Journal of Reproductive Immunology, Apr. 2007; 57(4):262-9 See Spec., pp. 4, 5 & 13 See International Search.
Van den Heuvel, et al., "Decline in Number of Elevated Blood CD3(+) CD56(+) NKT Cells in Response to Intravenous Immunoglobulin Treatment Correlates with Successful Pregnancy", American Journal of Reproductive Immunology, Nov. 2007; 58(5):447-59 See Spec., pp. 4 & 5 (To Follow).
Coulam et al., "Vascular Endothelial Growth Factor Gene Polymorphisms and Recurrent Pregnancy Loss", American Journal of Reproductive Immunology, Apr. 2008; 59(4):306-15 See Spec., p. 5 (To Follow).
Paparistidis et al., "How Valuable in Measurement of Peripheral Blood Natural Killer Cells at the Time of Abortion", American Journal of Reproductive Immunology, vol. 59, Issue 4, Feb. 21, 2008 See Spec., p. 5.
Perricone, et al., "High Levels of Peripheral Blood NK Cells in Women Suffering from Recurrent Spontaneous Abortion are Reverted from High-Done Intravenous Immunoglobulins", American Journal of Reproductive Immunology, Mar. 2006; 55(3):232-9 See Spec., p. 5 (To Follow).
Heilmann et al., "CD3– CD56+ DC16– Natural Killer Cells and Improvement of Pregnancy Outcome in IVF/ICSI Failure After Additional IVIG-Treatment", American Journal of Reproductive Immunology, Mar. 2010, 63(3):263-5 See Spec., p. 5 (To Follow).
Kane et al., "Determination of Natural Killer Cell Function by Flow Cytometry", Clinical and Diagnostic Laboratory Immunology, May 1996, pp. 295-300 See Spec., pp. 7 & 13.
Valiathan et al., "Evaluation of Flow Cytometry-Based Assay for Natural Killer Cell Activity in Clinical Settings", Scandinavian Journal of Immunology, Dec. 2011, vol. 75, Issue 4 See Spec., pp. 7 & 13 (To Follow).
Roussev et al., "Duration of Intralipid's Suppressive Effect on NK Cell's Functional Activity", American Journal of Reproductive Immunology, Sep. 2008; 60(3):258-63 See Spec., p. 12.
Juman et al., "Effects of Long-Term Oral Administration of Arachidonic Acid and Docosahexaenoic Acid on the Immune Functions of Young Rats", Nutrients, vol. 5, No. 6, May 29, 2013, pp. 1949-1961 See International Search.
Braverman, "Intralipid Therapy for Recurrent Pregnancy Loss—Controversies and Future Directions" 34th Annual Meeting of the American Society for Reproductive Immunology, Jun. 2-5, 2014 See International Search.
Yamashita et al, "Inhibition of Natural Killer Cell Activity by Eicosapentaenoic Acid in Vivo and In Vitro", Biochemical and Biophysical Research Communications, Elsevier, Amsterdam, NL, vol. 150, No. 1, Jan. 15, 1988, pp. 497-505 See International Search.
Yaqoob et al., Inhibition of Natural Killer Cell Activity by Dietary Lipids:, Immunology Letters, Elsevier Bv, NL, vol. 41, No. 2-3, Jul. 1, 1994, pp. 241-247 See International Search.
Rizvi et al., "The Role of Vitamin E in Human Health and Some Diseases", Sultan Qaboos University Med,, vol. 14, pp. 157-165, May 2014.
Orsavova et al., "Fatty Acids Composition of Vegetable Oils and Its Contribution to Dietary Energy Intake and Dependence of Cardiovascular Mortality on Dietary Intake of Fatty Acids", International Journal of Molecular Sciences, vol. 16, pp. 12871-12890, Jun. 5, 2015.
International Search Report Corresponding to PCT/GR2017/000064 dated Jan. 16, 2018.
Written Opinion Corresponding to PCT/GR2017/000064 dated Jan. 16, 2018.

* cited by examiner

ORAL COMPOSITION WITH IMMUNOMODULATING EFFECT ON NATURAL KILLER CELLS

FIELD OF THE INVENTION

The present invention relates to oral compositions for use in a method for the treatment of repeated spontaneous abortions (RSA) or repeated implantation failures (RIF) after in vitro fertilization (IVF) in sub-fertile human female subjects having increased number and/or cytotoxicity of NK cells.

BACKGROUND OF THE INVENTION

Natural Killer (NK) cells are a specific group of large granular lymphocytes (LGL) which play a major role in innate immune responses but are also important in influencing adaptive immune responses and in immune regulation (Herberman R B. Role of human natural killer cell responses in health and disease. Olin Diagn Lab Immunol 1994; 1:125-33). They form 1-2% of lymphoid tissue found mainly in spleen. In the peripheral blood, NK cells make up 5-15% of all lymphocytes and 70-95% of LGLs (Stites D P, Terr A I, Parslow T G. Basic and clinical immunology. 8th edition, Appleton and Lange, Norwalk, Conn, 1994).

NK cells express on their surface a series of markers, the most characteristic of which are the molecules CD16 and CD56 (Caligiuri M. Human natural killer cells. Blood. 2008; 112:461-9). Based on the relative expression of CD16 and CD56, NK cells can be subdivided into different subpopulations. The two major subsets are CD56dim CD16bright (low expression of CD56, high expression of CD16), and CD56bright CD16dim/− (high expression of CD56, low or no expression of CD16). CD56dim CD16bright cells, which represent at least 90% of all peripheral blood NK cells, have cytotoxic function. Upon activation, they release perforin and granzyes from their granules, while they move to inflammation sites in response to chemokines released during inflammation by endothelial and innate immune cells (Moretta A, Marcenaro E, Parolini S, Ferlazzo G, Moretta L. NK cells at the interface between innate and adaptive immunity. Cell Death Differ 2008; 15:226-33). CD56bright CD16dim/− cells constitute the majority of NK cells in secondary lymphoid tissues, they are only weakly cytotoxic before activation, but, upon the effect of cytokines, they immediately produce large amounts of INF-γ and may have immunoregulatory properties (Poli A, Michel T, Theresine M, Andres E, Hentges F, Zimmer J, CD56bright natural killer (NK) cells: an important NK cell subset. Immunology 2009 April; 126(4):458-65). These cells constitute the major cell population of endometrial leukocytes (CD56 eGL: endometrial granulocytes), possibly after local differentiation (Hiby SE1, King A, Sharkey A M, Loke Y W, Human uterine NK cells have a similar repertoire of killer inhibitory and activatory receptors to those found in blood, as demonstrated by RT-PCR and sequencing, Mol Immunol. 1997 April; 34(5):419-30).

NK-like cells ($CD56^{bright}$ $CD16^{dim/-}$) are the dominant decidual cell population from the first stages of pregnancy through the first trimester. There is evidence that their proliferation and differentiation is synchronized with the secretory phase of the menstrual cycle when estrogens and progesterone prepare the endometrium for a prospective pregnancy. During this phase, uterine stromal leukocytes increase highly (25% from 5%) as a result of NK cell influx from blood or other tissues or of reprogramming and differentiation of endometrial stromal cells to NK cells (Gellersen B, Brosens I A, Brosens J J. Decidualization of the human endometrium: mechanisms, functions, and clinical perspectives. Semin Reprod Med 2007; 25:445-53. Santoni A, Carlino C, Gismondi A. Uterine NK cell development, migration and function. Reprod Biomed Online 2008; 16:202-10). If pregnancy occurs, NK-like cells increase rapidly and are distributed broadly throughout decidua found in close proximity to extravillous trophoblast (King A. Uterine leukocytes and decidualization. Hum Reprod Update 2000; 6:28-36). Due to their increased presence and direct contact with invading trophoblast, they have been considered as important for the establishment of normal pregnancy. There is evidence that, coincident with blastocyst implantation and decidualization, uterine NK cells become activated, they produce IFN-γ, perforin and other molecules, including angiogenetic factors, so that they may control trophoblast invasion through their cytotoxic activity, and also initiate vessel instability and remodelling of decidual arteries to increase the blood supply to the feto-placental unit (Ashkar A A, Di Santo J P, Croy B A. Interferon gamma contributes to initiation of uterine vascular modification, decidual integrity, and uterine natural killer cell maturation during normal murine pregnancy. J Exp Med 2000; 192: 259-70). Furthermore, decidual NK cells may be involved in cytokine-mediated immunoregulation of the maternal immune response producing Th2-type cytokines and growth factors, which result in placental augmentation and local immunosuppression and immunomodulation (Clark D, Arck P C, Jallili R, et al. Psycho-Neuro-Cytokine/Endocrine pathways in immunoregulation during pregnancy. Am J Reprod Immunol 1996; 35:330-7Chaouat G, Tranchot Diallo J, Volumenie J L, et al. Immune suppression and Th1/Th2 balance in pregnancy revisited: A (very) personal tribute to Tom Wegmann. Am J Reprod Immunol 1997; 37:427-34).

Decidual NK cells appear to be the main cell population involved in cases of the so called alloimmune abortions where the embryo is recognized as foreign and is "rejected" by the mother (Labarrere C A. Allogeneic recognition and rejection reactions in the placenta. Am J Reprod Immunol 1989; 21:94-9 Stern J J, Coulam C B: Current status of immunologic recurrent pregnancy loss. Curr Opin Obstet Gynecol 1993; 5:252-9). Under the influence of Th1-type cytokines they are stimulated to become classical NK cells expressing CD16 ($CD56^{dim}$ $CD16^{bright}$), which can damage trophoblast either directly by releasing cytolytic substances or indirectly by producing inflammatory cytokines (King A, Wheeler R, Carter N P, et al. The response of human decidual leukocytes to IL-2. Cell Immunol 1992; 141:409-42).

Clinical studies have demonstrated that women who tend to abort have increased numbers of NK cells of the conventional CD3-CD56+CD16+ type in the uterus. (Vassiliadou N, Bulmer J N: Immunohistochemical evidence for increased numbers of 'classic' CD57+ natural killer cells in the endometrium of women suffering spontaneous early pregnancy loss. Hum Reprod 1996; 11:1569-74 Kwak J Y, Beer A E, Kim S H, et al. Immunopathology of the implantation site utilizing monoclonal antibodies to natural killer cells in women with recurrent pregnancy losses. Am J Reprod Immunol 1999; 41:91-8), as well as increased blood NK subsets and NK cell activity, all of which have been associated with abortion of chromosomally normal embryos (Coulam C B, Goodman C, Roussev R G, et al. Systemic CD56+ cells can predict pregnancy outcome. Am J Reprod Immunol 1995; 33:40-6 Aoki K, Kajiura S, Matsumoto Y, et al. Preconceptual natural killer cell activity as a predictor of miscarriage. Lancet 1995; 345:1340-2).

Because of the above data, the increased numbers and/or cytotoxicity of peripheral blood NK cell ($CD56^{bright}$ $CD16^{dim/-}$) are used in practice for the diagnosis of alloimmune abortions and as markers for the selection of women for immunotherapy (Coulam C B, Goodman C, Roussev R G, et al. Systemic CD56+ cells can predict pregnancy outcome. Am J Reprod Immunol 1995; 33:40-6 Aoki K, Kajiura S, Matsumoto Y, et al. Preconceptual natural killer cell activity as a predictor of miscarriage. Lancet 1995; 345:1340-2).

Classically, the main therapies to reduce detrimental NK cell activation and prevent abortions and/or RIF have been active immunization of the women using paternal or third party lymphocytes (Gafter U, Sredni B, Segal J, Kalechman Y. Suppressed cell-mediated immunity and monocyte and natural killer cell activity following allogeneic immunization of women with spontaneous recurrent abortion. J Clin Immunol 1997; 17:408-19), and passive immunization in the form of intravenous administration of immunoglobulin G (IVIg) (Ruiz J E, Kwak J Y, Baum L, et al. Intravenous immunoglobulin inhibits natural killer cell activity in vivo in women with recurrent spontaneous abortion. Am J Reprod Immunol 1996; 35:370-5). Some known side effects or adverse events of Intravenous Immunoglobulin are: Aseptic meningitis, renal failure, thromboembolism, haemolytic reactions, anaphylactic reactions, lung disease, enteritis, dermatologic disorders and infectious diseases (Stiehm, 2013). An alternative treatment proposed during the last years to suppress NK cell functional cytotoxicity, is the intravenous administration of fat emulsions (ex, Intralipid®) comprising purified soya been oil, purified egg phospholipid, glycerol anhydrous and water for injection which is usually used as a source of energy and of essential fatty acids in patients with nutritive or other disorders requiring parenteral nutrition (Natural killer cell functional activity suppression by intravenous immunoglobulin, Intralipid and soluble human leukocyte antigen-G. Am J Reprod Immunol 2007; 57:262-9, Meng L, Lin J, Chen L, Wang Z, Liu M, Liu Y, Chen X, Zhu L). The treatment with Intralipid® reduces the cytotoxicity of the peripheral blood NK cells, but it does not reduce the number of peripheral blood NK cells. Furthermore intravenous infusion of Intralipid® may cause several side effects such as bladder pain, bloody or cloudy urine, chills, difficult, burning, or painful urination, fever, frequent urge to urinate, lower back or side pain, sore throat and vomiting. Recent research has shown that intravenous administration of Intralipid® can cause hepatomegaly, jaundice, cholestasis, splenomegaly, thrombocytopenia, leukopenia and fat overload syndrome (<1% in clinical trials) (FDA, 2007).

Both the increased number and the increased cytotoxicity of peripheral blood NK cells can cause recurrent spontaneous abortions (Am J Reprod Immunol. 2007 November; 58(5):447-59. Decline in number of elevated blood CD3(+) CD56(+) NKT cells in response to intravenous immunoglobulin treatment correlates with successful pregnancy, van den Heuvel M J1, Peralta C G, Hatta K, Han V K, Clark D A; An Increased N K-cell percentage 5 days after the pregnancy termination could be a marker of immune aetiology of miscarriage, as the probability of an aborter with NK>12% to have an immune-mediated abortion is almost 90%. Am J Reprod Immunol. 2008 April; 59(4):306-15. doi: 10.1111/j.1600-0897.2007.00547.x. Epub 2008 Feb. 21).

It has been shown that the measurement of peripheral blood NK cells at the time of abortion is valuable and due to the significant role of elevated NK cells number. (Paparistidis N1, Papadopoulou C, Chioti A, Papaioannou D, Tsekoura C, Keramitsoglou T, Kontopoulou-Antonopoulou V, Agapitos E, Balafoutas C, Varla-Leftherioti M).

A number of studies have shown that the reduction of peripheral NK cells number and activity results to an important improvement in live birth rate that rises in very high levels Am J Reprod Immunol. 2006 March; 55(3):232-9; High levels of peripheral blood NK cells in women suffering from recurrent spontaneous abortion are reverted from high-dose intravenous immunoglobulins (Perricone R1, Di Muzio G, Perricone C, Giacomelli R, De Nardo D, Fontana L, De Carolis C. Am J Reprod Immunol. 2010 Mar. 1; 63(3):263-5. doi: 10.1111/j.1600-0897.2009.00790.x. Epub 2010 Jan. 8; CD3-CD56+CD16+ natural killer cells and improvement of pregnancy outcome in IVF/ICSI failure after additional IVIG-treatment. Heilmann L1, Schorsch M, Hahn T. Am J Reprod Immunol. 2007 April; 57(4):262-9; Natural killer cell functional activity suppression by intravenous immunoglobulin, intralipid and soluble human leukocyte antigen-G. Roussev R G1, Ng S C, Coulam C B. (Am J Reprod Immunol. 2007 November; 58(5):447-59; Decline in number of elevated blood CD3(+) CD56(+) NKT cells in response to intravenous immunoglobulin treatment correlates with successful pregnancy. Van den Heuvel M J1, Peralta C G, Hatta K, Han V K, Clark D A).

The above mentioned treatments, have a number of drawbacks and disadvantages. For example, they require repeated hospitalizations of the patients as well as permanent doctor's surveillance. Furthermore, since the patients are hospitalized, they may be exposed to hospital-acquired infections. In addition, these methods are associated with the risks and side effects of intervention treatments (including life-threatening ones such sepsis from human derived products, hypercoagulation from fat emulsion infusions). In addition, these treatments are associated with serious side effects.

The present invention addresses these issues and provides a number of advantages compared to the prior art.

SUMMARY OF THE INVENTION

The present invention provides oral compositions comprising a combination of fatty acids or esters thereof, for use by women who experience recurrent spontaneous abortions (RSA) or repeated implantation failures (RIF) in the in vitro fertilization (IVF) setting and have increased number and/or cytotoxicity of peripheral blood NK cells.

The compositions of the present invention comprise as active ingredients a combination of fatty acids or esters thereof and they are administered in certain amounts and over a certain period of time.

Accordingly, the present invention aims to prevent immune-mediated sub-fertility in a considerably significant cohort of couples facing related problems, which apart from the family status, depriving them the opportunity to give birth to a child, could have also considerable social, psychological and economical impact.

DETAILED DESCRIPTION OF THE INVENTION

It has now surprisingly been found that an oral composition comprising a mixture of fatty acids or esters thereof administered in certain amounts and over a certain period of time reduces the number and cytotoxicity of peripheral NK cells in women experiencing recurrent spontaneous abortions (RSA) or repeated implantation failures (RIF) and having increased numbers of peripheral blood NK cells and/or increased peripheral blood NK cell cytotoxicity.

Thus, the present invention provides an oral composition comprising as active ingredients a combination of fatty acids or esters thereof, for use in a method for the treatment of recurrent spontaneous abortions or repeated implantation failures in a human female subject having 12% or more of peripheral blood NK cells in total peripheral blood cells and/or wherein the cytotoxicity of the peripheral blood NK cells of the human female subject is at least 10% higher than the mean cytotoxicity of a control population of healthy human females of reproductive age with no reproductive failures and who have given birth to at least one child, wherein the composition is orally administered for 15 to 70 days and wherein the total amount of fatty acids or esters thereof administered per day is from 0.03 g/kg of body weight to 1 g/kg of body weight, calculated as fatty acids.

The present invention also provides a method for the treatment of recurrent spontaneous abortions or repeated implantation failures in a human female subject having 12% or more of peripheral blood NK cells in total peripheral blood cells and/or wherein the cytotoxicity of the peripheral blood NK cells of the human female subject is at least 10% higher than the mean cytotoxicity of a control population of healthy human females of reproductive age with no reproductive failures and who have given birth to at least one child, comprising administering to the human female subject an oral composition comprising as active ingredients a combination of fatty acids or esters thereof, wherein the composition is orally administered for 15 to 70 days and wherein the total amount of fatty acids or esters thereof administered per day is from 0.03 g/kg of body weight to 1 g/kg of body weight, calculated as fatty acids.

In order to evaluate the NK cell cytotoxicity, several methods can be applied. Although 51Cr release is the classical method for determining cytotoxicity, alternate methods are available and several other are in developmental stages. In laboratories where the use of radioactive isotopes is not desirable or permissible, or when using tumor target cells that do not readily take up the 51Cr label, test systems that utilize enzymes and colorimetric or fluorometric dyes could be employed. Today the most common method for the determination of NK cell activity is flow cytometry, a method which can be modified regarding the use of the reagents, nevertheless the result remains the same. (Determination of natural killer cell function by flow cytometry. Kimberly I. Kane et al, Clinical and diagnostic laboratory immunology, may 1996, p. 295-300; Evaluation of a Flow Cytometry-Based Assay for Natural Killer Cell Activity in Clinical Settings, R. Valiathan et al. 2011 The Authors. Scandinavian Journal of Immunology).

A person skilled in the art appreciates that the NK cytotoxicity normally may be inconsistent within an individual because of the many possible immunological and endocrine influences on NK cells. Therefore, minor changes in NK activity may be expected when repeatedly testing healthy individuals. A different control population could provide different mean NK cytotoxicity values. In order to have a statistically correct result the more the control samples are the better. Nevertheless, the present invention is applied to human female subjects having cytotoxicity of the peripheral blood NK cells at least 10% higher than the mean cytotoxicity of a control population of healthy human females of reproductive age with no reproductive failures, such as miscarriages or unsuccessful IVFs, and who have given birth to at least one child.

According to the present invention, the term "recurrent spontaneous abortions (RSA)" is defined as two or more spontaneous losses of pregnancy prior to the 20th gestational week of pregnancy.

According to the present invention, the term "repeated implantation failures (RIF)" is defined as the absence of implantation after two repetitive unsuccessful cycles of in vitro fertilization (IVF), or intracytoplasmic sperm injection (ICSI) or frozen embryo replacement cycles.

According to the present invention, increased cytotoxicity of peripheral blood NK cells is defined as any killing activity which is at least 10% higher than the mean cytotoxicity of a control population of healthy women of reproductive age with no reproductive failures, such as miscarriages or unsuccessful IVFs, and who have given birth to at least one child, The term "treatment of recurrent spontaneous abortions or repeated implantation failures" means a reduction of the risk of miscarriage of a treated subject compared to the risk she would have been exposed to had she not been treated, as well as an improvement of pregnancy outcome.

According to the present invention, the term "fatty acid" means an aliphatic monocarboxylic acid having a saturated or unsaturated chain, commonly comprising from 4 to 28 carbon atoms.

According to the present invention, the term "long chain fatty acid" means a fatty acid having an aliphatic chain of 13 or more carbon atoms.

According to the present invention, the term "medium chain fatty acid" means a fatty acid having an aliphatic chain of 6 to 12 carbon atoms.

According to the present invention, the term "short chain fatty acid" means a fatty acid having an aliphatic chain of less than 6 carbon atoms.

The compositions of the present invention comprise a combination of fatty acids or esters thereof. The fatty acids include short chain, medium chain or long chain, saturated or unsaturated fatty acids. Preferably, the compositions of the present invention comprise long chain fatty acids or long chain and medium chain fatty acids.

Examples of saturated long chain fatty acids include palmitic, stearic, myristic, and arachidic acid.

Examples of monounsaturated long chain fatty acids include oleic, docosahexaenoid (DHA), eicosapentaenoic (EPA), paimitoleic, myristoleic and sapienic acid.

Examples of polyunsaturated long chain fatty acids include linoleic, a-linolenic and γ-linolenic acid.

Examples of medium chain fatty acids include lauric, capric and caprilic acid.

Examples of short chain fatty acids include butanoic, 2-methylpropanoic, pentanoic and 3-methylbutanoic acid.

The fatty acid esters of the compositions of the present invention are esters of fatty acids with aliphatic alcohols, such as $C_1$-$C_6$ alcohols, glycerides, i.e. monoglycerides, diglycerides, or triglycerides, phospholipids, such as phosphatidic acids or phosphoglycerides, sphingolipids, saccharolipids, waxes and mixtures thereof. Preferably, the fatty acid esters are glycerides, phospholipids, sphingolipids or saccharolipids and mixtures thereof. More preferably, the fatty acid esters are glycerides.

According to the present invention, the term "calculated as fatty acids" means that when the composition comprises fatty acid esters, their amounts have to be converted to those of the corresponding fatty acids in order to determine the quantity of the oral composition to be administered.

Preferably, the compositions of the present invention comprise at least one saturated, at least one monounsaturated and at least one polyunsaturated long chain fatty acid or an ester thereof.

Preferably, at least 50% by weight of the active ingredients in the compositions of the present invention, calculated as fatty acids, are long chain fatty acids or esters thereof. More preferably, at least 65% by weight of the active ingredients in the compositions of the present invention, calculated as fatty acids, are long chain fatty acids or esters thereof. Even more preferably, at least 97% by weight of the active ingredients in the compositions of the present invention, calculated as fatty acids, are long chain fatty acids or esters thereof.

The fatty acids of the compositions of the present invention act as intracellular and intercellular mediators having various effects on immune and inflammatory responses where NK cells are involved. Fatty acids are involved through several mechanisms in the modulation of the immune system including (i) membrane fluidity; (ii) production of lipid peroxides; (iii) eicosanoid synthesis; and (iv) influence on gene regulation. It is possible that fatty acid immunomodulation occurs not only by the individual, but also by the collective action of these factors.

The compositions of the present invention may comprise additional active ingredients, such as vitamins, metal ions or amino acids. When these active ingredients are present, their total amount is preferably less than 6% of the total amount of active ingredients. Examples of vitamins include vitamins B1, B2, B3, B6, D, myo-inositol, inositol and folic acid. Metal ions may include for example selenium, magnesium, copper, zinc or manganese. Amino acids may include naturally occurring amino acid, such as L-arginine or L-glutamine. The vitamins, metal ions or amino acids do not contribute directly to a decrease in the number and/or the cytotoxic activity of the NK cells but contribute to the body's immune defenses by supporting physical barriers, cellular immunity and antibody production. Nevertheless there is a belief that the steroid hormone 1,25-dihydroxyvitamin D3 {1,25-(OH)2-D3} has immunosuppressive action.

The presence of vitamins in the compositions of the present invention exhibits an immune modulating and homeostatic effect to the environment where the NK cells are found. The aim is to create a favorable milieu and contribute to the improvement of the whole reproductive process, having a modulation of the maternal response by keeping the immune system in balance. However, increased level of vitamins may boost the immune system and increase the effect of the NK cells. For this reason, when vitamins are present in the compositions of the present invention, their total amount is preferably less than 4% of the total amount of active ingredients.

The compositions of the present invention may have any form suitable for oral administration. Such forms are well known to a person skilled in the art and they include liquid forms, such as oral solutions, oral suspensions or oral emulsions, oral gels or solid forms, such as tablets, capsules or sachets. The compositions of the present invention can be administered as nutritional supplements.

In addition to the active ingredients, the compositions of the present invention may comprise one or more pharmaceutically acceptable excipients well known in the art, such as binders, diluents, disintegrants, suspending agents, lubricants, solvents, emulsifiers, thickening agents, buffering agents, preservatives, sweeteners, colouring agents, flavouring agents and the like.

The compositions can be produced by processes well know to the person skilled in the art.

The compositions of the present invention are administered for 15 to 70 days. Preferably, the compositions are administered for 30 to 60 days. More preferably, the compositions are administered for 40 to 50 days.

The compositions of the present invention may be administered once per day or more than once per day, e.g. twice per day. Nevertheless, according to the present invention the total amount of fatty acids or esters thereof administered per day is from 0.03 g/kg of body weight to 1 g/kg of body weight, calculated as fatty acids. Preferably, the total amount of fatty acids or esters thereof administered per day is from 0.10 g/kg of body weight to 0.70 g/kg of body weight, calculated as fatty acids. More preferably, the total amount of fatty acids or esters thereof administered per day is from 0.20 g/kg of body weight to 0.50 g/kg of body weight, calculated as fatty acids.

The compositions of the present invention specifically decrease the number and cytotoxicity of the peripheral blood NK cells without overall suppression of the immune system.

With the present invention, both the NK cell's cytotoxicity and the NK cell percentage in total peripheral blood cells remain at low levels for 12-14 weeks after the discontinuation of the treatments, achieving a prolonged protection and prevention of RSA or RIF in sub-fertile women having increased number of peripheral blood NK cells and/or increased peripheral blood NK cells activity. This represents a great improvement over intravenous administration of Intralipid®, in which the effect ceases after 6-9 weeks from the discontinuation of the treatment (Acacio B, Ng S C, Coulam C B., Am J Reprod Immunol. 2008 September; 60(3):258-63. doi: 10.1111/j.1600-0897.2008.00621.x. Duration of intralipid's suppressive effect on NK cell's functional activity Roussev R G). Furthermore, the treatment with Intralipid® reduces the cytotoxicity of the peripheral blood NK cells, but it is not known to reduce the number of peripheral blood NK cells. In contrast, the present invention reduces both the number and the cytotoxicity of the peripheral blood NK cells. In addition, intravenous infusion of Intralipid® may cause several side effects such as bladder pain bloody or cloudy urine, chills, difficult, burning, or painful urination, fever, frequent urge to urinate, lower back or side pain, sore throat and vomiting, whereas the present invention does not show these side effects.

In contrast to the treatments of the prior art, in which intravenous or subcutaneous (lymphocyte immunization) infusions are applied, with the present invention the compositions are administered orally and its components are digested through the digestive tract and follow the normal process of food consumption and absorption. In this way, the treatment of RSA or RIF becomes easier and safer in comparison to the treatments of the prior art. Furthermore, with the present invention there is no need for hospitalization or permanent surveillance by doctors and protects women from exposure to hospital-acquired infections. In addition, the present invention is not associated with the risks and side effects of intervention treatments. Furthermore, with the present invention the reduction of the numbers and cytotoxicity of the peripheral blood NK cells last longer after the treatment is discontinued and a prolonged protection is achieved in comparison to the treatments of the prior art.

EXAMPLES

Examples 1-4 illustrate the effect of compositions of the present invention in the reduction of the number peripheral NK cells and their activity (cytotoxicity). The compositions were administered to healthy women of reproductive age (between 25-46 years old) experiencing RSA or RIF and having increased number of peripheral blood NK cells and increased peripheral blood NK cells activity. Blood samples from all women were tested at day zero before the initiation of the treatment, at day 45 and at day 70 depending on the case. All of them had a routine check 12 weeks after the discontinuation of the treatment.

The determination of the peripheral blood samples for NK cell percentage in total lymphoid cells and NK cell activity was performed by flow-cytometry using previously described techniques. (Determination of natural killer cell function by flow cytometry. Kimberly I. Kane et al, Clinical and diagnostic laboratory immunology, may 1996, p. 295-300; Evaluation of a Flow Cytometry-Based Assay for Natural Killer Cell Activity in Clinical Settings, R. Valiathan et al. 2011 The Authors. Scandinavian Journal of Immunology). This method gives the percentage of target cells killed by natural cytotoxic cells present in PBL. Two fluorescent dyes are used to discriminate between effector and target cells and between live and dead target cells. One is a green fluorescent dye, 3,3'-Dioctadecyloxacarbocyanine perchlorate (DiO) which is used to label the plasma membranes of K562, a human erythroleukaemic tumor cell line used as the target population. The second dye propidium iodide (PI), a membrane impermeable, red fluorescent dye, which is added during the assay when targets cells membranes were disrupted by NK-like cells. Intact target cells unaffected by effectors were single positive (and exhibited only green fluorescence), while targets killed by effectors bearing disrupted membranes are double positive (and exhibited green as well as red fluorescence). Effector and target cells are added in tubes to create different effector-to-target (E:T) ratios, 1:50, 1:25 and 1:12.5. In the following examples the results are presented at E:T ratios 50:1.

(Natural killer cell functional activity suppression by intravenous immunoglobulin, intralipid and soluble human leukocyte antigen-G. Roussev R G1, Ng S C, Coulam C B. Am J Reprod Immunol. 2007 April; 57(4):262-9.).

Control samples were healthy women of reproductive age with no reproductive failures such as miscarriages or unsuccessful IVFs and who have given birth to at least one child. Based upon the healthy control population, mean NK cytotoxicity was 19% in 50:1 ratio.

Changes in NK cell cytotoxicity and number from day 0 to day 70 were measurable by the above mentioned assay. During the administration of the compositions of the invention, baseline mean percentage NK cell activity and number was significantly decreased after 45 days and then declined close to its baseline levels after 70 days. A repeated measurement after the administration of the oral compositions showed significant decrease on both the number as well as the cytotoxicity of the NK cells.

In the examples below, the following abbreviations are used:
LCFA— Long chain fatty acids
SFA— Saturated fatty acids
MUFA— Monounsaturated fatty acids
PUFA— Polyunsaturated fatty acids
MCFA— Medium chain fatty acids.

Example 1

A group of 15 women was treated once per day with oral composition 1 in the form of oral solution comprising the active ingredients shown in Table 1a. The fatty acids of the composition were in the form of glycerides. The amount of the administered composition was such that the total amount of fatty acids administered per day was 0.25 g/kg of body weight. Blood samples were collected and tested prior to and 45 days after the initiation of the treatment.

TABLE 1a

| % Active substances | | | |
|---|---|---|---|
| LCFA 97.64% | SFA 14.74% | Miristic acid | 0.20% |
| | | Palmitic acid | 4.50% |
| | | Stearic acid | 10.04% |
| | MUFA 23.39% | Oleic acid | 21.39% |
| | | Docosahexaenoid acid (DHA) | 0.50% |
| | | Eicosapentaenoic acid(EPA) | 1.50% |
| | PUFA 59.51% | Linoleic acid | 49.27% |
| | | γ-linolenic | 0.50% |
| | | α-linolenic | 9.74% |
| Vitamins 1.64% | | B1 | 0.02% |
| | | B2 | 0.02% |
| | | B3 | 0.02% |
| | | B6 | 0.01% |
| | | D3 (15 µg-600 IU) | 0.48% |
| | | Folic Acid | 0.03% |
| | | Myo-inositol | 1.06% |
| Metal ions 0.10% | | Cooper | 0.01% |
| | | Zinc | 0.02% |
| | | Magnesium | 0.06% |
| | | Manganium | 0.01% |
| Aminoacids | | L-Glutamin | 0.62% |

The results of the numbers and activity of peripheral blood NK cells are shown in Table 1 b.

TABLE 1b

| | Day 0 NK % number (mean) | Day 45 NK % number (mean) | Mean Decline % | Day 0 NK Activity | Day 45 NK Activity | Mean activity Decline % |
|---|---|---|---|---|---|---|
| (45 days) | | | | | | |
| Subjects 15 | 20.25 | 13.59 | 31 | 46.26 | 18.54 | 59.92 |

The average percentage of peripheral blood NK cells in total peripheral blood cells was 20.25 on day 0 before the treatment and 13.59 on day 45 after the beginning of the treatment. This difference was statistically significant (p value<0.0001).

The average activity of peripheral blood NK cells at 50:1 ratio was 46.26 on day 0 before the treatment and 18.54 on day 45 after the beginning of the treatment. This difference was statistically significant (p value<0.0001).

Five women of the above-mentioned group continued the treatment for a total of 70 days. They were tested at day 70 for peripheral blood NK cell numbers and activity. The results are shown in Table 1c.

TABLE 1c

| | Day 0 NK % number (mean) | Day 70 NK % number (mean) | Mean Decline % | Day 0 NK Activity | Day 70 NK Activity | Mean activity Decline % |
|---|---|---|---|---|---|---|
| (70 days) | | | | | | |
| Subjects 5 | 18.42 | 11.45 | 37.41 | 46.54 | 13.60 | 70.43 |

The average percentage of peripheral blood NK cells in total peripheral blood cells was 18.42 at day 0 before the treatment and 11.45 at 70 days after the beginning of the treatment. This difference was statistically significant (p value<0.0001).

The average activity of peripheral blood NK cells at 50:1 ratio was 46.54 at day 0 before the treatment and 13.60 at 45 days after the beginning of the treatment. This difference was statistically significant (p value<0.0001).

All women treated with this composition are currently pregnant.

Example 2

A group of 6 women were tested at day 0 and at day 70 for NK cell number and activity after administration of oral composition 2 once per day. The composition was in the form of oral solution comprising the active ingredients shown in Table 2a. The fatty acids of the composition were in the form of glycerides. The amount of the administered composition was such that the total amount of fatty acids administered per day was 0.25 g/kg of body weight.

TABLE 2a

| | | % active substances | |
|---|---|---|---|
| LCFA 97.84% | SFA 11.29% | Miristic acid | 3.05% |
| | | Palmitic acid | 6.84% |
| | | Steatic acid | 1.40% |
| | MUFA 35.85% | Oleic acid | 28.85% |
| | | Docosahexaenoid acid (DHA) | 1.80% |
| | | Eicosapentaenoic acid(EPA) | 5.20% |
| | PUFA 50.70% | Linoleic acid | 29.28% |
| | | γ-linolenic | 18.69% |
| | | α-linolenic | 2.73% |
| MCFA 2% | | Capric acid | 0.50% |
| | | Caprilyc acid | 0.50% |
| | | Lauric acid | 1.00% |
| Vitamins 0.16% | | D3 | 0.10% |
| | | Folic acid | 0.03% |
| | | Myo-inositol | 0.03% |

The results of the numbers and activity of peripheral blood NK cells are shown in Table 2b.

TABLE 2b

| | Day 0 NK % number (mean) | Day 70 NK % number (mean) | Mean Decline % | Day 0 NK % Mean Activity | Day 70 NK % Mean Activity | Mean activity Decline % |
|---|---|---|---|---|---|---|
| Subjects 6 | 18.45 | 12.80 | 30.62 | 43.32 | 19 | 56.14 |

The average percentage of peripheral blood NK cells in total peripheral blood cells was 18.45 on day 0 before the treatment and 12.80 on day 70 after the beginning of the treatment. This difference was statistically significant (p value 0.001).

The average activity of peripheral blood NK cells at 50:1 ratio was 43.32 on day 0 before the treatment and 19, on day 70 after the beginning of the treatment. This difference was statistically significant (p value 0.001).

Example 3

In this group 6 patient's blood samples were collected and tested prior to and at 45 days after administration of oral composition 3 once per day. The composition was in the form of oral solution comprising the active ingredients shown in Table 3a. The fatty acids of the composition were in the form of glycerides. The amount of the administered composition was such that the total amount of fatty acids administered per day was 0.25 g/kg of body weight.

TABLE 3a

| | | % active substances | |
|---|---|---|---|
| LCFA 100% | SFA 25% | Miristic acid | 10% |
| | | Palmitic acid | 10% |
| | | Steatic acid | 5% |
| | MUFA 50% | Oleic acid | 22% |
| | | Docosahexaenoid acid (DHA) | 6% |
| | | Eicosapentaenoic acid(EPA) | 19% |
| | | Miristoleic acid | 0.2% |
| | | Palmitoleic acid | 2.6% |
| | | Sapienic acid | 0.2% |
| | PUFA 25% | Linoleic acid | 12% |
| | | γ-linolenic | 5% |
| | | α-linolenic | 8% |

The results of the numbers and activity of peripheral blood NK cells are shown in Table 3b.

TABLE 3b

| | Day 0 NK % number (mean) | Day 45 NK % number (mean) | Mean Decline % | Day 0 NK % Activity Day 0 | Day 45 NK % Activity Day 70 | Mean activity Decline % |
|---|---|---|---|---|---|---|
| Subjects 6 | 17.84 | 12.40 | 30.48 | 36 | 16.6 | 53.88 |

The average percentage of peripheral blood NK cells in total peripheral blood cells was 17.84 on day 0 before the treatment and 12.40 on day 45 after the beginning of the treatment. This difference was statistically significant (p value<0.001).

The average activity of peripheral blood NK cells at 50:1 ratio was 36 on day 0 before the treatment and 16.6 on day 45 after the beginning of the treatment. This difference was statistically significant (p value 0.001).

Three out of the six women treated with this composition have given birth and 2 are pregnant.

Example 4

In this group 8 patient's blood samples were collected and tested prior to and 45 days after administration of oral composition 4 once per day. The composition was in the form of oral solution comprising the active ingredients shown in Table 4a. The fatty acids of the composition were in the form of glycerides. The amount of the administered composition was such that the total amount of fatty acids administered per day was 0.25 g/kg of body weight.

TABLE 4a

| | | % active substances | |
|---|---|---|---|
| LCFA 65% | SFA 6.43% | Miristic acid | 1.00% |
| | | Palmitic acid | 3.00% |
| | | Steatic acid | 1.40% |
| | MUFA 45.71% | Oleic acid | 45.71% |

TABLE 4a-continued

| | | % active substances | |
|---|---|---|---|
| | PUFA 12.86% | Linoleic acid | 10.03% |
| | | γ-linolenic acid | 1.93% |
| | | α-linolenic acid | 1.93% |
| MCFA 30.71% | | Capric acid | 5.00% |
| | | Caprilyc acid | 8.71% |
| | | Lauric acid | 17.00% |
| Vitamins 3.06% | | D3 | 0.80% |
| | | B1 | 0.11% |
| | | B2 | 0.11% |
| | | B3 | 0.13% |
| | | B6 | 0.11% |
| | | Folic Acid | 0.10% |
| | | Inositol | 1.7% |
| Metal ions 0.83% | | Cooper | 0.10% |
| | | Zinc | 0.13% |
| | | Magnesium | 0.50% |
| | | Manganium | 0.10% |
| Aminoacids 1.04% | | L-Glutamin | 0.54% |
| | | L-Arginine | 0.50% |

The results of the numbers of peripheral blood NK cells are shown in Table 4b.

TABLE 4b

| Subjects 8 | Day 0 NK % number (mean) | Day 45 NK% number (mean) | Mean 10% Decline |
|---|---|---|---|
| | 18.97 | 14.55 | 23.29 |

The average percentage of peripheral blood NK cells in total peripheral blood cells was 18.97 on day 0 before the treatment and 14.55 on day 45 after the beginning of the treatment. This difference was statistically significant (p value<0.017).

Five of the eight women treated with this oral composition have given birth to healthy children, 2 are currently pregnant after the 25th week and 1 has aborted.

The invention claimed is:

1. A method of treating immune-mediated recurrent spontaneous abortions or repeated implantation failures in a human female subject having at least one of 12% or more of peripheral blood NK cells in total peripheral blood cells, and a cytotoxicity of the peripheral blood NK cells of the human female subject that is at least 10% higher than a mean cytotoxicity of a control population of healthy human females of reproductive age with no reproductive failures and who have given birth to at least one child, the method comprising:
   providing a composition, comprising, as active ingredients:
   a combination of fatty acids or esters thereof,
   administering the composition orally, to the human female subject, for 15 to 70 days, wherein a total amount of fatty acids or esters thereof administered per day is from 0.03 g/kg of body weight to 1 g/kg of body weight, calculated as fatty acids;
   thereby reducing immune-mediated sub-fertility for the human female subject.

2. The method of treating immune-mediated recurrent spontaneous abortions or repeated implantation failures in a human female subject according to claim 1, wherein the total amount of fatty acids or esters thereof administered per day is from 0.10 g/kg of body weight to 0.70 g/kg of body weight, calculated as fatty acids.

3. The method of treating immune-mediated recurrent spontaneous abortions or repeated implantation failures in a human female subject according to claim 2, wherein the total amount of fatty acids or esters thereof administered per day is from 0.20 g/kg of body weight to 0.50 g/kg of body weight, calculated as fatty acids.

4. The method of treating immune-mediated recurrent spontaneous abortions or repeated implantation failures in a human female subject according to claim 1, wherein the composition is administered for 30 to 60 days.

5. The method of treating immune-mediated recurrent spontaneous abortions or repeated implantation failures in a human female subject according to claim 1, wherein the composition is administered for 40 to 50 days.

6. The method of treating immune-mediated recurrent spontaneous abortions or repeated implantation failures in a human female subject according to claim 1, wherein the fatty acids are selected from the group consisting of long chain, medium chain and short chain fatty acids and mixtures thereof.

7. The method of treating immune-mediated recurrent spontaneous abortions or repeated implantation failures in a human female subject according to claim 6, wherein the long chain fatty acids are selected from the group consisting of palmitic, stearic, myristic, arachidic, oleic, docosahexaenoid, eicosapentaenoic, palmitoleic, myristoleic, sapienic, linoleic, a-linolenic, γ-linolenic acid and mixtures thereof.

8. The method of treating immune-mediated recurrent spontaneous abortions or repeated implantation failures in a human female subject according to claim 6, wherein the medium chain fatty acids are selected from the group consisting of lauric, capric, caprilic acid and mixtures thereof.

9. The method of treating immune-mediated recurrent spontaneous abortions or repeated implantation failures in a human female subject according to claim 1, wherein the composition comprises at least one saturated, at least one monounsaturated and at least one polyunsaturated long chain fatty acid or esters thereof.

10. The method of treating immune-mediated recurrent spontaneous abortions or repeated implantation failures in a human female subject according to claim 1, wherein at least 50% by weight of the active ingredients in the composition, calculated as fatty acids, are long chain fatty acids or esters thereof.

11. The method of treating immune-mediated recurrent spontaneous abortions or repeated implantation failures in a human female subject according to claim 10, wherein at least 65% by weight of the active ingredients in the composition, calculated as fatty acids, are long chain fatty acids or esters thereof.

12. The method of treating immune-mediated recurrent spontaneous abortions or repeated implantation failures in a human female subject according to claim 11, wherein at least 97% by weight of the active ingredients in the composition, calculated as fatty acids, are long chain fatty acids or esters thereof.

13. The method of treating immune-mediated recurrent spontaneous abortions or repeated implantation failures in a human female subject according to claim 1, wherein the fatty acid esters are selected from the group consisting of monoglycerides, diglycerides, triglycerides, phospholipids, sphingolipids, saccharolipids and mixtures thereof.

14. The method of treating immune-mediated recurrent spontaneous abortions or repeated implantation failures in a human female subject according to claim 1, wherein the fatty acid esters are selected from the group consisting of monoglycerides, diglycerides, triglycerides and mixtures thereof.

15. The method of treating immune-mediated recurrent spontaneous abortions or repeated implantation failures in a human female subject according to claim 1, wherein the composition further comprises one or more vitamins, metal ions, amino acids or mixtures thereof.

* * * * *